(12) United States Patent
Desvaux De Marigny

(10) Patent No.: US 11,413,181 B2
(45) Date of Patent: Aug. 16, 2022

(54) MODULAR DEVICE FOR DORSAL PROTECTION

(71) Applicant: EVOM, Saint Clement de Riviere (FR)

(72) Inventor: Christopher Desvaux De Marigny, Saint Clement de Riviere (FR)

(73) Assignee: EVOM, Saint Clement de Riviere (FR)

( * ) Notice: Subject to any disclaimer, the term of this patent is extended or adjusted under 35 U.S.C. 154(b) by 0 days.

(21) Appl. No.: 14/892,490

(22) PCT Filed: May 22, 2014

(86) PCT No.: PCT/FR2014/051204
§ 371 (c)(1),
(2) Date: Nov. 19, 2015

(87) PCT Pub. No.: WO2014/188132
PCT Pub. Date: Nov. 27, 2014

(65) Prior Publication Data
US 2016/0113804 A1    Apr. 28, 2016

(30) Foreign Application Priority Data

May 23, 2013    (FR) ..................................... 13 54649

(51) Int. Cl.
*A61F 5/02*    (2006.01)
*A61F 5/01*    (2006.01)
(Continued)

(52) U.S. Cl.
CPC .................. *A61F 5/02* (2013.01); *A61F 5/01* (2013.01); *A61G 5/1091* (2016.11); *A61G 5/122* (2016.11)

(58) Field of Classification Search
CPC .. A61F 5/02; A61F 5/022; A61F 5/028; A61F 5/01; A61F 5/0102; A61F 5/024;
(Continued)

(56) References Cited

U.S. PATENT DOCUMENTS

| 4,658,807 A | 4/1987 | Swain |
| 2006/0181126 A1 | 8/2006 | Eysing |

(Continued)

FOREIGN PATENT DOCUMENTS

| EP | 0109572 A1 | 5/1984 |
| WO | 96 07344 A1 | 3/1996 |

(Continued)

*Primary Examiner* — Tarla R Patel
(74) *Attorney, Agent, or Firm* — Craft Chu PLLC; Andrew W. Chu

(57) ABSTRACT

The modular device for dorsal protection suitable to be worn by a wearer includes at least two holding elements arranged one beneath the other and suitable for receiving, on the front face thereof, the back of the wearer. The holding elements are interconnected, in pairs, on the rear face thereof, by at least one hinged connection, each hinged connection ensuring the link between two adjacent holding elements. Each hinged connection includes at least two degrees of torsional freedom and bending freedom such that each holding element and each hinged connection or joining part moves in relation to the other under the action of the movements of the wearer, while ensuring that the device is maintained in contact with the back of the wearer.

13 Claims, 1 Drawing Sheet

(51) Int. Cl.
*A61G 5/10* (2006.01)
*A61G 5/12* (2006.01)

(58) Field of Classification Search
CPC ........... A61F 5/026; A61G 5/12; A61G 5/122;
A61G 5/1091; A47C 1/024; A47C 1/032;
A47C 3/025; A47C 3/12; A47C 1/03261;
A47C 7/14; A47C 7/44; A47C 7/36;
A47C 7/402; A47C 7/566; A47C 16/005;
A47C 20/027
USPC ................................................ 602/19; 601/5
See application file for complete search history.

(56) References Cited

U.S. PATENT DOCUMENTS

2010/0268137 A1* 10/2010 Bachmann ............ A61F 5/0102
602/16
2012/0157901 A1* 6/2012 Galante ................... A61G 5/12
602/19

FOREIGN PATENT DOCUMENTS

| WO | 02 22067 A1 | 3/2002 |
| WO | 2012 149978 A1 | 11/2012 |
| WO | 2013 174484 A1 | 11/2013 |

* cited by examiner

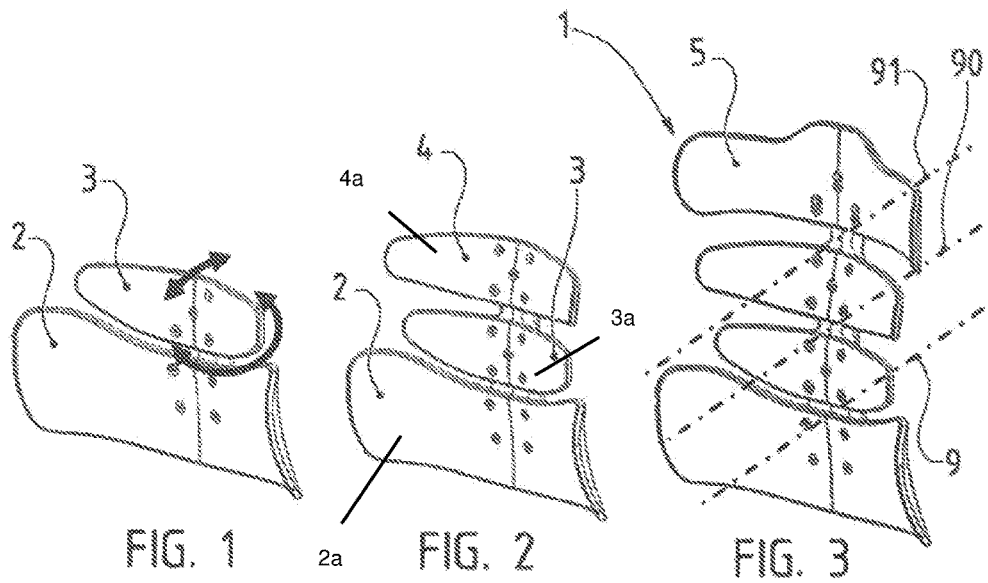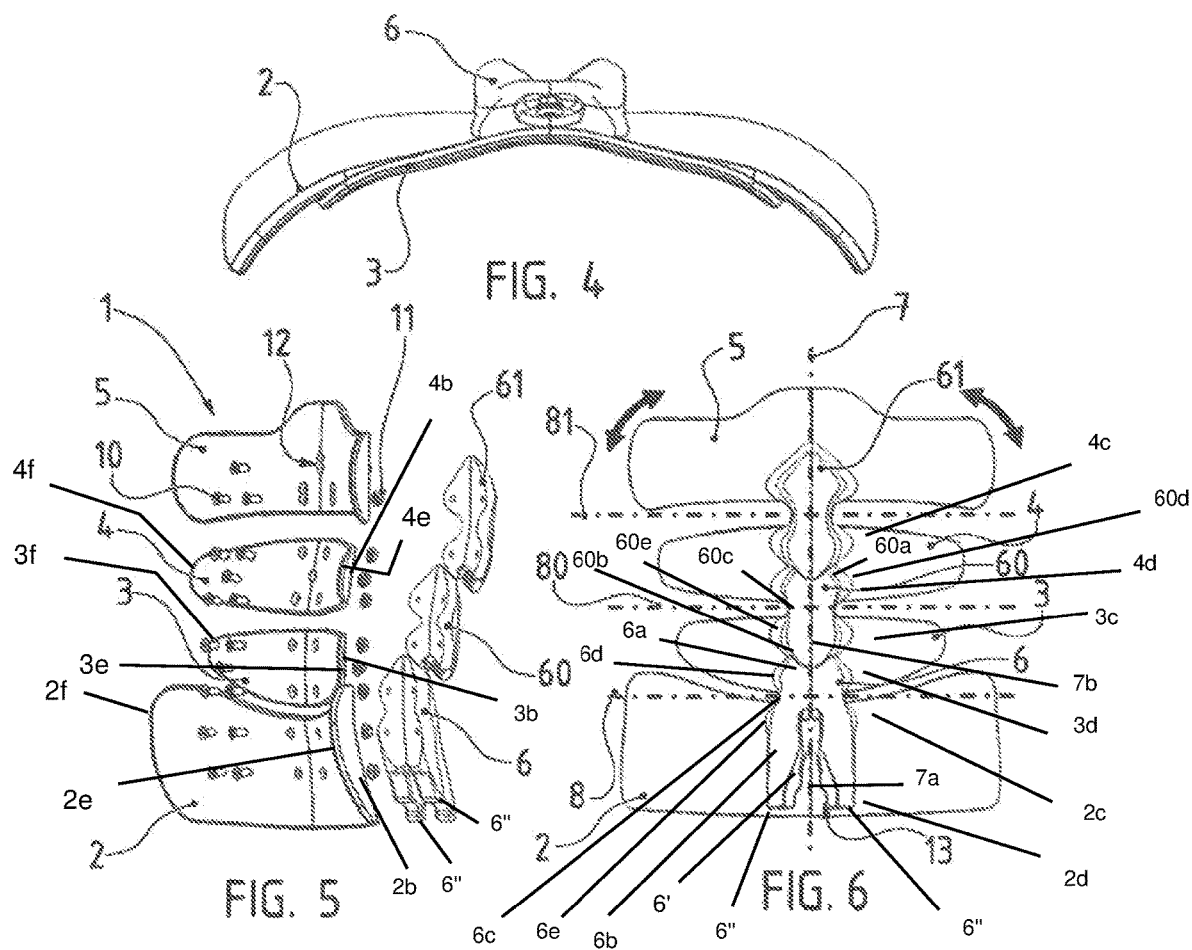

MODULAR DEVICE FOR DORSAL PROTECTION

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention is related to the field of dorsal protections.

The invention relates in particular to a hinged modular device for dorsal protection.

Such a device will find a preferred, but in no way restrictive application in the medical and paramedical field, in the form of an external protective shell intended to be fastened and held to the back of a patient, in the way of an orthosis, but designed hinging so as to permit, but especially to improve, the movements of said patient.

It should be noted that such a protection device can be used to match a person with reduced mobility, forming a personal hinged back for the user, likely to replace or supplement the back of his wheelchair.

2. Description of Related Art Including Information Disclosed Under 37 CFR 1.97 and 37 CFR 1.98

As is known, a person with reduced mobility, whose movements require a wheelchair, is facing the rigidity of the back against which he remains resting. Presently, the backs the wheelchairs are provided with are straight and rectilinear, fully ill-adapted to the morphology of the back having a globally S-shape, provided with its kyphosis and lordosis. Therefore, the prolonged rest against a straight and static back causes painful disc diseases. In addition, this rigidity results into a certain immobility of the patient, preventing or limiting the dorsal movements necessary for the intervertebral discs to maintain their flexibility, and to thus continue to play their role as shock absorbers.

On the other hand, a paralysis, which a person with reduced mobility suffers from, causes muscle atrophy. Therefore, the lack of effort and physical activity results into a lack of oxygenation of the body cells. Under such circumstances, the resting against the back does not occur uniformly at the level of the whole surface of the patient's back, but at limited resting points located at the level of the spinous processes of the spine, which have become more prominent.

Another drawback resides in the prolonged impact of inertia of resting in nearly permanent contact at the level of the skin of the back. The dermis and epidermis are then compressed. The contact prevents the skin from breathing properly, causing numbness that can go as far as tissue ischemia and the risk of developing pressure ulcers. Furthermore, in order to compensate for the muscle loss, a person with reduced mobility has to wear a lap belt in order to keep the viscera all around his belly, directly into contact with the skin. Such a belt rubs and forms folds, making its wearing constraining and uncomfortable. In addition, the resting related to the folds at the level of the lower back may in the long run cause an adverse change in positions of the lumbar vertebrae of the spine.

In order to reduce the drawbacks due to the prolonged positioning, a dorsal wedge can be arranged between the person's back and the back of the chair, at the level of the lumbar vertebrae. However, this wedge, which is more like a cushion, is connected neither to the chair nor to the person, so that it moves and does not maintain its position, thus generating discomfort.

In order to try to cope with these disadvantages, an existing solution consists of wheelchairs provided with an ergonomic seat and back, provided with a padded layer. This equipment is often heavy and expensive, improving only comfort without actually treating the fundamental constraints related to the position of the back of the human body. There are also chairs, the back of which has at the bottom a hinge permitting its rotation from a vertical position into positions inclined rearwards, and vice versa. This change of position requires a constraining, even tedious manipulation by the person on a maneuvering organ. In addition, the inclined positions do not provide a comfortable sitting, just permitting the person to apply a temporary relaxing effect of his back to relieve pressures on the intervertebral discs.

An alternative solution consists of a dorsal shell, similar to a medical corset. An example of such a shell is described in WO 96/07344. It is comprised of a rigid frame on which curved blades made of flexible material are fixed laterally. Suitable means ensure the deformation of the blades by an external pressure from said fixed and rigid frame. It is thus possible to adjust the shape of said blades depending on the patient's back morphology. In addition, a central vertical panel has a bending following the lumbar curve of the back. Such a shell thus ensures a holding of the back, with a very fine adjustment. However, once in place, this corset constitutes a unique rigid shell, not permitting any movement of the back. In additional, the flat shape of the vertical panel also gives rise to the disadvantages of pressing on the tips of the spinous processes and of compression of the skin.

Another example of a shell is described in EP 0 109 572. It also comprises a fixed armature receiving, fixed to same, plates made of deformable material, so as to be bent in order to match the anatomical morphology of the person. The aim of this shell is to fix and hold some parts of the body of a patient, namely with a view to his recovery or his rehabilitation. Here too, this shell is similar to a corset, which, once positioned, permits no freedom of movement of the wearer, generating more disadvantages than the straight back of a wheelchair.

BRIEF SUMMARY OF THE INVENTION

The aim of the present invention is to cope with the disadvantages of the prior art by providing a hinged modular device for dorsal protection.

To this end, first of all, such a device is designed modular, provided with several holding elements completely dissociated from each other. Depending on the number of elements, a holding may be ensured from the lumbar level of the lower back to the dorsal, even cervical level. Preferably, said device comprises at least two holding elements. Thus, it is possible to adapt the number of elements depending on the person who will wear it and his disability.

Furthermore, each holding element has an ergonomic shaped generally curved in the form of an arc of a circle, following the rounded shape of the back along its width. In this respect, depending on the position at the level of which each element rests against the back, each element then has different dimensions, wider at the lumbar, chest and upper dorsal levels and less wide at the lower dorsal level. In addition, the shape of an arc of a circle may have, at the central level, a recess provided for receiving the projection of the spinous processes of the spine, ensuring a support essentially on both sides of the latter. Thus, this anthropomorphic shape perfectly adapts to the back of the person. In addition, each element may be made of a rigid or semi-rigid material, permitting only a limited deformation through bending or separation of the ends of its holding elements (a deformed position by bending the ends, a deformed position by separating those ends). Thus, the latter are very well resting against and independently hold each part of the back.

In addition, it is possible to apply the device directly against the skin of the back, under the clothes, serving as an interface with the back against which the person rests, but also with the fabric, avoiding causing folds and friction.

On the other hand, an essential feature of this device lies in the hinging of its holding elements. Indeed, the invention provides to permit the movement of the holding elements relative to each other with at least two degrees of freedom of movement, in torsion and in bending. Thus, the wearer can turn only part of his back, the shoulders relative to the pelvis, while maintaining the protection in place against the back. He can also stretch himself by arching the back, while connecting with the device.

In addition, the joints between each element are designed elastic, so as to permit their deformation, but to apply a force, of elastic restoring into the original position. Thus, the wearer's movements receive a constraint, requiring an effort, which maintains and ensures muscle development, while promoting the movements of part of the back and, therefore, maintaining the elasticity of the intervertebral discs.

Furthermore, said joints permit to provide a space between the then separated holding elements, preventing them from touching or rubbing against each other during their respective displacements.

Therefore, the shell device according to the invention constitutes a hinged protection specific for each person and configured for the morphology of his back, connected in the manner of an orthosis.

Alternatively, this dorsal protection may constitute a back, when it is provided, in its lower portion, with means for a removable fastening to said chair. Therefore, the person can at will secure his dorsal protection to the chair, or detach it from same, providing a presently unmatched freedom of movement for a person with reduced mobility.

In addition, since this dorsal protection can be applied directly against the skin, it is possible to wear it under the clothes.

More particularly, the hinged modular device for dorsal protection comprises at least a first lower element and a second upper element for holding and supporting the back connected to each other at the rear faces by means of at least one hinged connection.

It is characterized in that said connection comprises at least two degrees of torsional and bending freedom.

Moreover, according to further additional non-restricting features, said connection can be elastic.

According to one embodiment, said connection can be formed of a single joining part made of elastic material such as elastomer.

According to the preferred embodiment, said part may be made of polyurethane.

Advantageously, the device may comprise at least a third element connected in the upper portion to said second element through an identical hinged connection.

In particular, such a device may also comprise at least one fourth element connected in the upper portion to said third element through an identical hinged connection.

Furthermore, each element may be formed by a single blade curved at the front face.

According to another alternative feature, said link can form separation means spaced apart from said elements.

According to an additional feature, said first element comprises in the lower portion removable fastening means aimed at cooperating with complementary means provided at the level of a wheelchair, so that said device constitutes the back of same. Further features and advantages of the invention will become clear from the following detailed description of non-restrictive embodiments of the invention, with reference to the attached figures.

BRIEF DESCRIPTION OF THE SEVERAL VIEWS OF THE DRAWINGS

FIGS. 1 to 3 show perspective three-quarter views of three different embodiments of said device, in which the latter is provided with two, three and four holding elements, respectively.

FIG. 4 is a schematic view, showing the embodiment of the device of FIG. 2 in a view from above.

FIG. 5 is a perspective schematic view, showing the embodiment of FIG. 4 in an exploded view, showing the different parts forming it and the fastenings between them.

FIG. 6 is a schematic view, showing the embodiment of FIG. 4 in a view from behind.

DETAILED DESCRIPTION OF THE INVENTION

Such a device 1 is similar to a shell designed in several parts fastened relative to each other in order to permit their relative movements, while ensuring its maintaining into contact with the back of its wearer. In brief, the various parts have a determined mobility and can move relative to each other under the action of the movements of the user, in particular of the movements of the various parts of his back, like turning the shoulders or the upper torso relative to the pelvis, arching backward or leaning forward. To this end, said device comprises at least a first lower 2 and a second upper holding and dorsal supporting element 3. Depending on the back of its wearer, but also on his disability, said device 1 may comprise more holding elements 2, 3, namely at least two, three or four, or even more. FIG. 1 shows a device 1 provided with two holding elements 2, 3, while in FIG. 2 it comprises a third holding element 4, and in FIG. 3 this shell is comprised of a fourth holding element 5.

It should be noted that the first element 2 is always located in the lower portion of the device 1, aimed at being applied at the level of the bottom of the back, in front of the lumbar region, while the second element 3 is positioned just above, applied in the middle of the back, as the third element 4 is located above it, in the upper portion of the back, in front of the thoracic vertebrae.

In addition, an additional element, not shown, may be positioned further above, at the level of the cervical vertebrae. In addition, the device 1 pretends to be ergonomic and anthropomorphic. To this end, each element (first holding element 2, second element 3, third element 4, fourth element 5) is formed of a single blade curved at the front face. The first holding element 2 has a first front face 2a, a first rear face 2b having a first upper end 2c and a first lower end 2d, and first ends 2e, 2f. The second holding element 3 has a second front face 3a, a second rear face 3b having a second upper end 3c and a second lower end 3d, and second ends 3e, 3f. The third holding element 4 has a third front face 4a, a third rear face 4b having a third upper end 4c and a third lower end 4d, and third ends 4e, 4f. In brief, each holding element can be formed by a respective blade having a curvature along an arc of a circle extending so as to form a rounded concavity at the corresponding first front face, second front face, third front face, etc., for receiving the back of the wearer.

In addition, this concavity may comprise, at the central level, a recess formed by a discontinuity in the uniformity of the curvature of the blade. This recess is oriented rearwards, forming protrusions on both sides. Said recess is aimed at receiving the spinous processes of the spine, while said protrusions rest on both sides of the latter.

This configuration, particularly visible in FIG. 4, thus permits to improve the comfort and the support of the back against and within said device.

In addition, each blade constituting an element may have dimensions in length but also in height, as well as a curvature adapted to the portion of the back against which it is aimed at resting.

Essentially, two elements are connected to each other at the rear faces through at least one hinged connection 6. Thus, in the case of two elements 2 and 3, they are connected by a single connection 6. In the case three elements 2, 3 and 4, they are connected in pairs by two connections 6 and 60. In the case of four elements 2, 3, 4 and 5, they are connected in pairs by three connections 6, 60 and 61.

In particular, as visible in FIGS. 5 and 6, the connection 60 (or 61) of a pair of upper elements 3 and 4 (or 5 and 6, respectively) may overlap at least partially, from the rear, the connection 6 (or 60, respectively) of a couple of elements 2 and 3 (or 3 and 4, respectively) located below.

According to a preferred feature, each connection 6, 60, 61 constitutes separating means spaced apart from said elements. In brief, it connects its pair of elements 2 and 3, 3 and 4, 4 and 5, so as to provide a space between them, in order to permit their relative displacement without any risk that said materials touch or rub against each other, namely at the level of their respective edges.

According to an essential feature, each hinged connection 6, 60, 61, including the first joining part 6 and the second joining part 60, has at least two degrees of torsional and bending freedom. In other terms, each connection 6, 60, 61 permits the rotation of two elements with respect to each other, on the one hand, about a first virtual axis 7 passing through said connection or first joining part 6 as a vertical first dorsal axis 7, second joining part 60 as a vertical second dorsal axis 7, and a third joining part 61 and extending substantially vertically and, on the other hand, about a second virtual axis 8 passing approximately through the center of said connection or first joining part 6 as a horizontal first dorsal axis 8, second joining part 60 as a horizontal second dorsal axis 80, and a third joining part 61 as a horizontal third dorsal axis 81 and extending substantially horizontally and approximately in the respective first dorsal bearing plane of the first joining part 6 or second dorsal bearing plane of the second dorsal bearing plane of the second joining part 60.

It should be noted that said first axis 7 (vertical first dorsal axis 7a is the portion of first axis 7 for first joining part 6, vertical second dorsal axis 7b is the portion of first axis 7 for second joining part 60) is identical for all the connections (the first joining part 6, the second joining part 60, and the third joining part 61), while each connection 6, 60, 61 has a second independent axis 8, 80, 81 specific to it.

These two rotations are modeled in FIG. 1, while FIG. 6 shows the six axes.

In brief, the rotation about the first axis 7 of a joining part 6, 60, 61 permits the rotation of each element 2, 3, 4 (first holding element 2 in front of the vertical first dorsal axis 7a, second holding element 3 in front of the vertical second dorsal axis 7b, third holding element 4 in front of the vertical third dorsal axis 7c) as a respective first rotated position, etc., when the wearer turns part of his back, such as the shoulders or the torso relative to the pelvis. In addition, the rotation about one and/or the other of said second axes 8, 80, 81 of a joining part 6, 60, 61 permits the rotation of each element 2, 3, 4 (first holding element 2 in front of the horizontal first dorsal axis 8, second holding element 3 in front of the horizontal second dorsal axis 80, third holding element 4 in front of the horizontal third dorsal axis 81) as a respective second rotated position, when the wearer moves to arch backward or to lean forward.

According to a particular embodiment, said hinged connection 6, 60, 61 can have a third virtual axis or normal first dorsal axis 9, normal second dorsal axis 90, normal third dorsal axis 91 extending approximately orthogonally to the respective first and second dorsal bearing planes containing the vertical first dorsal axis 7 and horizontal first dorsal axis 8 and the vertical second dorsal axis 7 and the horizontal second dorsal axis 80, respectively, so as to define a first dorsal bearing space and a second dorsal bearing space, respectively.

Such rotation is shown in FIG. 6 for the fourth element 5 and corresponds to a movement of the upper torso when the wearer bends to the right or to the left. Such a movement can apply at the level of the connections 6, 60, 61 of each pair of elements, each having a third axis 9, 90, 91. The rotation about one and/or the other of the third axes 9, 90, 91 of a joining part 6, 60, 61 similarly permits the rotation of each element 2, 3, 4 (first holding element 2 in front of the normal first dorsal axis 9, second holding element 3 in front of the normal second dorsal axis 90, third holding element 4 in front of the normal third dorsal axis 91) as a respective third rotated position.

Thus, each connection 6, 60, 61 is similar to a multi-axis link.

According to an additional feature, said connection 6, 60, 61 can be designed resilient. In other words, it applies a force (a first rotation restoring force, a second rotation restoring force, a third rotation restoring force) for elastic restoring into the original position during the various rotations (first rotated position, second rotated position, third rotated position) and movements of the elements with respect to each other, induced by the movements of the wearer. Said original position corresponds to the device 1 as shown in the figures, when it is placed so as to support and hold the back of its wearer, without any stress on the connections 6, 60, 61, so that the back of said wearer is held in a natural position.

Moreover, the resilient nature of each connection 6, 60, 61 can be obtained through the material it is formed of. To this end, said connection 6, 60, 61 consists of a single joining part made of elastic material such as elastomer. Such a material ensures the deformation of said part, then its restoring into the original shape.

According to the preferred embodiment, said part may be made of polyurethane. This material has the required characteristics of elasticity, for increased resistance to deformation, as well as good strength over time and less wear.

As is visible in FIGS. 5 and 6, each part, such as the first joining part 6 and second joining part 60, may have a specific elongate shape from a lower end, such as lower first end portion 6*b* and lower second end portion 60*b* to an upper end, such as upper first end portion 6*a* and upper second end portion 60*a*. At each of these ends, said part is wider, forming lugs, such as an upper first end lug 6*d* and upper second end lug 60*d*, and a lower first end lug 6*e* and lower second end lug 60*e*. in front of the elements against the rear face of which they rest and are fastened to. In short, the central portion of each part, such as first central portion 6*c* of the first joining part 6 and second central portion 60*c* of the second joining part 60, has a narrowing, convergent toward the instantaneous center of the above-mentioned rotations.

In addition, said parts are fastened to each of these two elements, as well as, according to the preferred embodiment, overlap the lower part.

To this end, said device 1 comprises fastening means in the form of at least one pair of screw 10 and nut 11. This pair passes through each element in order to cooperate with each other. In particular, each screw 10 passes through an element, at the level of a through hole 12, from its front face to the rear face, in order to cooperate by screwing with the corresponding nut 11.

It should be noted that each hole 12 may have a chamfered edge so that the head of said screw 10 is flush with the surface of the front face of the element, which it passes through.

In addition, according to the preferred embodiment, each nut 11 is included within the part constituting the connection 6, 60, 61. To this end, at the time of the manufacturing, said nuts 11 are molded directly inside said part, ending on the side of the face resting against and into contact with the rear face of each element, in front of the openings 12.

In this respect, it should be noted that said contact face of each part is designed curved, having a concavity, so as to match the convex rounded shape of the rear face of the elements against which it is fastened.

As mentioned above, said device 1 may comprise two elements 2 and 3. It may also comprise at least a third element 4 connected in the upper portion to said second element 3 through a hinged connection 60 identical to the connection 6, i.e. it has the same characteristics, in particular elastic characteristics, but it may be of a different shape and size. Likewise, the device may comprise at least a fourth element 5 connected in the upper portion to said third element 4 through an identical hinged connection 61, i.e. it has the same characteristics, in particular elastic characteristics, but may be of a different shape and size.

Furthermore, said device 1 may comprise means for securing to the back of its wearer. Such means, not shown, may be in the form of straps, secured at one end to one and/or the other of said elements, depending on their number. These straps can be joined at their respective opposite end, then forming a harness ensuring the holding in place of said device 1, but also its holding into contact and resting against the back of the wearer. In this respect, said device can be covered at least partly with a coating, in particular a cover, in order to improve the comfort of its wearing into contact with the skin. Such a cover then has dimensions adapted to the device, in particular to the number of elements it includes.

According to another possible embodiment, each element may receive a complementarily shaped coating, such as a cushioning in the form of removable cushions, even a cover.

According to a preferred embodiment, at least the first element 2 may comprise a lap belt, surrounding the belly of its wearer. This belt is then fastened to each element, in particular at the level of its distal ends. Thus, said belt only supports the belly from the front, without applying any force on the rear of the back, at the level of the lumbar region. This force is transmitted to the element, which it is fastened to.

According to an additional feature, said first element 2 can comprise, in the lower portion, removable fastening means 13 aimed at cooperating with complementary means (not shown) provided for at the level of a wheelchair, so that said device 1 constitutes the back.

These means 13 may be of any shape and permit to hook the complementary means, namely by snap-connection. An unlocking system is then provided in order to unlock this hooking.

Thus, the device 1 according to the invention provides a modular protective shell, through the number of elements 2, 3, 4, 5, which can constitute it, in order to adapt to the morphology and the dorsal stresses of the wearer. It is also ergonomic because of its shape. Primarily, it permits the movements of its wearer, applying an elastic pressure, ensuring the restoring into an optimal position for holding the back in a natural position, but providing a resistance permitting to maintain the muscle tonus of the back of its wearer.

I claim:

1. A modular device for dorsal protection, comprising:
    a first holding element (2) having a first front face (2*a*), a first rear face (2*b*) having a first upper end (2*c*) and a first lower end (2*d*), and first ends (2*e*, 2*f*);
    a second holding element (3) having a second front face (3*a*), a second rear face (3*b*) having a second upper end (3*c*) and a second lower end (3*d*), and second ends (3*e*, 3*f*);
    a third holding element (4) having a third front face (4*a*), a third rear face (4*b*) having a third upper end (4*c*) and a third lower end (4*d*), and third ends (4*e*,4*f*), said second holding element (3) being located above said first holding element (2), said third holding element (4) being above said second holding element (3) and said first holding element (2), said second holding element (3) being between said first holding element (2) and said third holding element (4);
    a first joining part (6) connecting said first upper end (2*c*) of said first rear face (2*b*) to said second lower end (3*d*) of said second rear face (3*b*) so as to define a first dorsal bearing plane, said first joining part (6) being comprised of a first resilient material, said first dorsal bearing plane having a vertical first dorsal axis (7a) and a horizontal first dorsal axis (8) orthogonal to said vertical first dorsal axis (7a); and a second joining part (60) connecting said second upper end (3c) of said second rear face (3b) to said third lower end (4d) of said third rear face (4b) so as to define a second dorsal bearing plane, said second joining part (60) being comprised of a second resilient material, said second dorsal bearing plane having a vertical second dorsal axis (7b) and a horizontal second dorsal axis (80) orthogonal to said vertical second dorsal axis (7b), said second resilient material being the same as said first resilient material, wherein said first holding element (2) is coplanar with said second holding element (3) in front of said first dorsal bearing plane in an original position, wherein said second holding element (3) is coaxial with said first holding element (2) in front of said vertical first dorsal axis (7a) and said vertical second dorsal axis (7b) in a first rotated position in front of said vertical first dorsal axis (7a) and said vertical second dorsal axis (7b), said first joining part (6) having a first rotation restoring force about said vertical first dorsal axis (7a) in a direction for said second holding element (3) from said first rotated position to said first original position, wherein said second ends (3e, 3f) of said second holding element (3) are capable of being deformed relative to each other in a deformed position by bending toward each other, wherein said second holding element (3) is coaxial with said first holding element (2) in front of said vertical first dorsal axis (7a) and said vertical second dorsal axis (7b) in a second rotated position in front of said vertical first dorsal axis (7a) and said vertical second dorsal axis (7b), said first joining part (6) having a second rotation restoring force about said horizontal first dorsal axis (8) in a direction for said second holding element (3) from said second rotated position to said original position, wherein said first joining part (6) is comprised of an elongate shape having a first central portion (6c), an upper first end portion (6a) being wider than said first central portion (6c) and forming an upper first end lug (6d), and a lower first end portion (6b) being wider than said first central portion (6c) and forming a lower first end lug (6e), wherein said second joining part (60) is comprised of an elongate shape having a second central portion (60c), an upper second end portion (60a) being wider than said second central portion (60c) and forming an upper second end lug (60d), and a lower second end portion (60b) being wider than said second central portion (60c) and forming a lower second end lug (60e), and wherein said upper first end portion (6a) overlaps said lower second end portion (60b).

2. The modular device for dorsal protection, according to claim 1, wherein said second ends (3e, 3f) of said second holding element (3) are capable of being deformed relative to each other in a deformed position by separation from each other, wherein said first joining part (6) has a normal first dorsal axis 9 orthogonal to said first dorsal bearing plane so as to define a first dorsal bearing space by said vertical first dorsal axis 7a, said horizontal first dorsal axis 8, and said normal first dorsal axis 9, wherein said second joining part (60) has a normal second dorsal axis 90 orthogonal to said second dorsal bearing plane so as to define a second dorsal bearing space by said vertical second dorsal axis 7b, said horizontal second dorsal axis 80, and said normal second dorsal axis 90, and wherein said second holding element (3) is coaxial with said first holding element (2) in front of said vertical first dorsal axis (7a) and said vertical second dorsal axis (7b) in a third rotated position in front of said vertical first dorsal axis (7a) and said vertical second dorsal axis (7b), said first joining part (6) having a third rotation restoring force about said normal first dorsal axis (9) in a direction for said second holding element (3) from said third rotated position to said original position.

3. The modular device for dorsal protection, according to claim 1, wherein said first joining part (6) is comprised of polyurethane, having a first elasticity.

4. The modular device for dorsal protection, according to claim 1, wherein said lower first end lug (6e) is aligned on said first upper end (2c) of said first rear face (2b) of said first holding element (2), wherein said upper first end lug (6d) is aligned on said second lower end (3d) of said second rear face (3b) of said second holding element (3), and wherein said first central portion (6c) is between said first holding element (2) and said second holding element (3).

5. The modular device for dorsal protection, according to claim 1, wherein said first joining part (6) comprises two parallel vertical arms defining a median vertical groove (6').

6. The modular device for dorsal protection, according to claim 1, further comprising a fastening means for said first holding element (2) and said first joining part (6), said fastening means being comprised of a screw (10) and a nut (11).

7. The modular device for dorsal protection, according to claim 6, wherein said nut (11) is made integral with said first joining part (6), and wherein said nut (11) has a face contacting said first upper end (2c) of said first rear face (2b).

8. The modular device for dorsal protection, according to claim 1, further comprising: a removable fastening means for said first holding element (2), said removable fastening means being mounted on said first rear face (2b).

9. The modular device for dorsal protection, according to claim 8, further comprising: a wheelchair with a complementary removable fastening means, said removable fastening means and said complementary removable fastening means being configures in a snap fit relation.

10. The modular device for dorsal protection, according to claim 1, further comprising: securing means for said first holding element (2), said second holding element (3), and said third holding element (4), said securing means being mounted on a distal end of said first holding element (2).

11. The modular device for dorsal protection, according to claim 10, wherein said securing means is comprised of an abdominal belt fastened to said distal end of said first holding element (2).

12. The modular device for dorsal protection, according to claim 1, wherein said first holding element (2) is comprised of a first blade, said first front face (2a) being curved, wherein said second holding element (3) is comprised of a second blade, said second front face (3a) being curved, and wherein said third holding element (4) is comprised of a third blade, said third front face (4a) being curved.

13. The modular device for dorsal protection, according to claim 12, wherein said first blade is comprised of a first recess centered on said first front face (2a), wherein said second blade is comprised of a second recess centered on said second front face (3a), and wherein said third blade is comprised of a third recess centered on said third front face (4a).

\* \* \* \* \*